United States Patent
Tombuelt-Meyer et al.

(10) Patent No.: US 9,693,909 B2
(45) Date of Patent: Jul. 4, 2017

(54) METHOD AND APPARATUS FOR MAKING PERSONAL HYGIENE ABSORBENT ARTICLES

(71) Applicant: The Procter & Gamble Company, Cincinnati, OH (US)

(72) Inventors: Thomas Tombuelt-Meyer, Nettersheim (DE); Rodrido Rosati, Frankfurt am Main (DE)

(73) Assignee: The Procter & Gamble Company, Cincinnati, OH (US)

( * ) Notice: Subject to any disclaimer, the term of this patent is extended or adjusted under 35 U.S.C. 154(b) by 660 days.

(21) Appl. No.: 13/849,571

(22) Filed: Mar. 25, 2013

(65) Prior Publication Data

US 2013/0260978 A1    Oct. 3, 2013

(30) Foreign Application Priority Data

Mar. 29, 2012  (EP) .................. EP12162251
Dec. 17, 2012  (EP) .................. EP12197408

(51) Int. Cl.
*A61F 13/15*    (2006.01)

(52) U.S. Cl.
CPC .. *A61F 13/15585* (2013.01); *A61F 13/15764* (2013.01); *A61F 13/15804* (2013.01); *A61F 2013/15813* (2013.01)

(58) Field of Classification Search
CPC ......... A61F 13/15585; A61F 13/15601; B65G 47/244; B65G 47/71

(Continued)

(56) References Cited

U.S. PATENT DOCUMENTS 2,254,290 A * 9/1941 Joa ................ B65G 47/244
                                                198/440
3,847,273 A * 11/1974 Buhayar ............ B65H 29/20
                                                198/377.07

(Continued)

FOREIGN PATENT DOCUMENTS

EP    0 149 880    7/1985
EP    1 947 037    7/2008

(Continued)

OTHER PUBLICATIONS

EP Search Report Application No. 12197408.3, dated Apr. 2, 2013, 10 pages.

(Continued)

*Primary Examiner* — Thanh Truong
*Assistant Examiner* — Patrick Fry
(74) *Attorney, Agent, or Firm* — Sarah M. DeCristofaro; Abbey A. Lopez

(57) ABSTRACT

A method and device for turning a continuous supply of absorbent cores oriented in cross machine direction into a machine direction orientation and dividing the supply of absorbent cores into two or more sub-lines is provided. The device includes a plurality of turning plates which each include means for picking up, holding and releasing the absorbent cores, means for reversibly transferring the turning plates from a core pick-up point to a core release point, each turning plate being mounted rotationally on an axis, so that the absorbent cores can be re-oriented from a cross-machine direction at the pick-up point into machine direction at the release point while being held on the turning plates. Each turning plate includes means for picking up, holding and releasing two or more absorbent cores.

16 Claims, 5 Drawing Sheets

(58) Field of Classification Search
USPC .................................................. 198/436, 441
See application file for complete search history.

(56) References Cited

U.S. PATENT DOCUMENTS

| | | | |
|---|---|---|---|
| 3,848,594 A | 11/1974 | Buell | |
| 3,860,003 A | 1/1975 | Buell | |
| 3,911,173 A | 10/1975 | Sprague, Jr. | |
| 3,929,135 A | 12/1975 | Thompson | |
| 4,164,997 A * | 8/1979 | Mueller | B65G 47/71 198/427 |
| 4,324,246 A | 4/1982 | Mullane et al. | |
| 4,340,706 A | 7/1982 | Obayashi et al. | |
| 4,342,314 A | 8/1982 | Radel et al. | |
| 4,463,045 A | 7/1984 | Ahr et al. | |
| 4,515,595 A | 5/1985 | Kievit et al. | |
| 4,573,986 A | 3/1986 | Minetola et al. | |
| 4,606,452 A * | 8/1986 | Lecrone | B65G 47/244 198/411 |
| 4,609,518 A | 9/1986 | Curro et al. | |
| 4,610,678 A | 9/1986 | Weisman et al. | |
| 4,617,082 A * | 10/1986 | Oshefsky | A61F 13/15609 156/164 |
| 4,629,643 A | 12/1986 | Curro et al. | |
| 4,662,875 A | 5/1987 | Hirotsu et al. | |
| 4,673,402 A | 6/1987 | Weisman et al. | |
| 4,681,793 A | 7/1987 | Linman et al. | |
| 4,695,278 A | 9/1987 | Lawson | |
| 4,697,691 A * | 10/1987 | Zodrow | B65G 47/681 198/418.5 |
| 4,699,622 A | 10/1987 | Toussant et al. | |
| 4,710,189 A | 12/1987 | Lash | |
| 4,785,996 A | 11/1988 | Ziecker et al. | |
| 4,795,454 A | 1/1989 | Dragoo | |
| 4,808,178 A | 2/1989 | Aziz et al. | |
| 4,834,735 A | 5/1989 | Alemany et al. | |
| 4,842,666 A | 6/1989 | Werenicz | |
| 4,846,815 A | 7/1989 | Scripps | |
| 4,888,231 A | 12/1989 | Angstadt | |
| 4,894,060 A | 1/1990 | Nestegard | |
| 4,909,803 A | 3/1990 | Aziz et al. | |
| 4,946,527 A | 8/1990 | Battrell | |
| 4,963,140 A | 10/1990 | Robertson et al. | |
| 5,006,394 A | 4/1991 | Baird | |
| 5,025,910 A * | 6/1991 | Lasure | A61F 13/15764 198/377.04 |
| 5,070,994 A * | 12/1991 | Focke | B65G 47/71 198/441 |
| 5,137,537 A | 8/1992 | Herron et al. | |
| 5,147,345 A | 9/1992 | Young et al. | |
| 5,151,092 A | 9/1992 | Buell et al. | |
| 5,221,274 A | 6/1993 | Buell et al. | |
| 5,242,436 A | 9/1993 | Weil et al. | |
| 5,260,345 A | 11/1993 | Desmarais et al. | |
| 5,342,338 A | 8/1994 | Roe | |
| 5,387,207 A | 2/1995 | Dyer et al. | |
| 5,499,978 A | 3/1996 | Buell et al. | |
| 5,507,736 A | 4/1996 | Clear et al. | |
| 5,535,999 A * | 7/1996 | Ford | B65H 29/38 198/377.03 |
| 5,554,145 A | 9/1996 | Roe et al. | |
| 5,556,504 A | 9/1996 | Rajala et al. | |
| 5,562,645 A | 10/1996 | Tanzer et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,591,152 A | 1/1997 | Buell et al. | |
| 5,607,760 A | 3/1997 | Roe | |
| 5,609,587 A | 3/1997 | Roe | |
| 5,635,191 A | 6/1997 | Roe et al. | |
| 5,643,588 A | 7/1997 | Roe et al. | |
| 5,830,202 A | 11/1998 | Bogdanski et al. | |
| 5,849,816 A | 12/1998 | Suskind et al. | |
| 5,865,823 A | 2/1999 | Curro | |
| 5,938,648 A | 8/1999 | LaVon et al. | |
| 5,968,025 A | 10/1999 | Roe et al. | |
| 6,004,306 A | 12/1999 | Robles et al. | |
| 6,375,769 B1 | 4/2002 | Quereshi et al. | |
| 6,432,098 B1 | 8/2002 | Kline et al. | |
| 6,450,321 B1 | 9/2002 | Blumenthal et al. | |
| 6,482,278 B1 * | 11/2002 | McCabe | A61F 13/15609 156/200 |
| 6,502,615 B1 | 1/2003 | Allen | |
| 6,632,504 B1 | 10/2003 | Gillespie et al. | |
| 6,645,569 B2 | 11/2003 | Cramer et al. | |
| 6,705,453 B2 | 3/2004 | Blumenthal et al. | |
| 6,716,441 B1 | 4/2004 | Osborne et al. | |
| 6,722,494 B2 * | 4/2004 | Nakakado | A61F 13/15764 198/377.01 |
| 6,811,019 B2 | 11/2004 | Christian et al. | |
| 6,848,566 B2 * | 2/2005 | Harnish | B65G 29/00 198/459.8 |
| 6,863,933 B2 | 3/2005 | Cramer et al. | |
| 6,946,585 B2 | 9/2005 | London Brown | |
| 7,112,621 B2 | 9/2006 | Rohrbaugh et al. | |
| 7,537,832 B2 | 5/2009 | Carlucci et al. | |
| 7,597,689 B2 * | 10/2009 | Hoffmann | A61F 13/495 604/378 |
| 7,750,203 B2 | 7/2010 | Busam et al. | |
| 7,770,712 B2 * | 8/2010 | McCabe | A61F 13/15764 198/463.1 |
| 7,786,341 B2 | 8/2010 | Schneider et al. | |
| 8,007,623 B2 * | 8/2011 | Andrews | A61F 13/15699 156/265 |
| 8,011,493 B2 * | 9/2011 | Giuliani | B65G 47/244 198/406 |
| 8,813,351 B2 * | 8/2014 | Schoultz | B65H 39/14 198/379 |
| 2002/0003021 A1 | 1/2002 | Maxton et al. | |
| 2003/0010438 A1 * | 1/2003 | Tharpe, Jr. | A61F 13/15764 156/297 |
| 2003/0084767 A1 | 5/2003 | Tanaka et al. | |
| 2003/0105190 A1 | 6/2003 | Diehl et al. | |
| 2003/0148684 A1 | 8/2003 | Cramer et al. | |
| 2004/0245069 A1 * | 12/2004 | Hook | A61F 13/15764 198/459.1 |
| 2005/0008839 A1 | 1/2005 | Cramer et al. | |
| 2005/0159720 A1 | 7/2005 | Gentilcore et al. | |
| 2007/0118087 A1 | 5/2007 | Flohr et al. | |
| 2007/0219521 A1 | 9/2007 | Hird et al. | |
| 2008/0312617 A1 | 12/2008 | Hundorf et al. | |
| 2008/0312622 A1 | 12/2008 | Hundorf et al. | |
| 2009/0192035 A1 | 7/2009 | Stueven et al. | |
| 2009/0258994 A1 | 10/2009 | Stueven et al. | |
| 2010/0012458 A1 | 1/2010 | Giuliana et al. | |
| 2010/0068520 A1 | 3/2010 | Stueven | |
| 2010/0192739 A1 | 8/2010 | Piantoni et al. | |
| 2011/0250413 A1 | 10/2011 | Lu et al. | |
| 2011/0268932 A1 | 11/2011 | Catalan et al. | |
| 2011/0319848 A1 | 12/2011 | McKiernan et al. | |

FOREIGN PATENT DOCUMENTS

| | | |
|---|---|---|
| GP | 2 297 955 | 8/1996 |
| JP | 61-183012 | 11/1986 |
| JP | 2005-126211 A | 5/2005 |
| WO | WO 95/16746 | 6/1995 |
| WO | WO 95/34329 | 12/1995 |
| WO | WO 99/34841 | 7/1999 |
| WO | WO 99/34842 | 7/1999 |
| WO | WO 02/064877 | 8/2002 |
| WO | WO 2005/079721 | 9/2005 |
| WO | WO 2006/014854 | 2/2006 |
| WO | WO 2006/015138 | 2/2006 |
| WO | WO 2006/015141 | 2/2006 |
| WO | WO 2006/083584 | 8/2006 |
| WO | WO 2007/047598 | 4/2007 |
| WO | WO 2010/001361 | 1/2010 |
| WO | WO 2011/163582 | 12/2011 |

(56) References Cited

FOREIGN PATENT DOCUMENTS

| WO | WO 2012/105374 | 8/2012 |
| WO | WO 2012/127954 | 9/2012 |

OTHER PUBLICATIONS

International Search Report PCT/US2013/033635, 15 pages.
EP Search Report, dated Sep. 3, 2012, 9 pages.

* cited by examiner

METHOD AND APPARATUS FOR MAKING PERSONAL HYGIENE ABSORBENT ARTICLES

CROSS REFERENCE TO RELATED APPLICATION

This application claims priority under 35 U.S.C. §119 to European Patent Application No. EP 12197408.3, filed Dec. 17, 2012, which claims priority to European Patent Application No. EP 12162251.8, filed Mar. 29, 2012, each of which are hereby incorporated by reference in its entirety.

FIELD OF THE INVENTION

The present disclosure relates to a method and apparatus for making disposable personal hygiene absorbent articles, and, in particular, a method and apparatus for making diapers or female sanitary pads.

BACKGROUND OF THE INVENTION

Disposable personal hygiene absorbent articles such as infant diapers or female sanity pads are mass-produced products. Modern processes allow the continuous production of these articles starting from the raw material (including pulp, superabsorbent polymers (SAP), nonwovens or films, elastic strings, etc.) to a finished bagged product ready for shipping on a single converting line. Complex article elements such as the absorbent cores can be pre-made at a supplier and then assembled to the other article elements at the converting line. In some processes, absorbent cores, especially for diapers, may be made in a core making apparatus directly feeding the converting line. The core making apparatus may lay down a mixture of cellulose pulp fibers and SAP to form the cores.

In some modern diaper converting processes, it may be possible to achieve a production speed in the order of 1000 diapers per minute. Modern converting lines are complex and very costly so that continuing development efforts are engaged to increase their production speed to maximize their production rate. However, in some processes, it has been difficult to increase the production speed over 1100 diapers per minute on a conventional manufacturing line because of processes limitations, in particular discrete transformations that cannot be made continuously such as intermittent gluing and application of discrete patches such as landing zones, ears, etc.

In some processes, absorbent cores may be oriented in cross-machine direction, assembled with certain article elements, and then turned in the machine direction for further converting on a single line. However, when the cores are turned in the machine direction, because the length to width ratio is usually of about 3:1, the downstream line speed needs to be accelerated to the same extent. This can create high mechanical forces during the turn and repitch operation that restraint the speed of the line achievable. In such design, line speed of 700 units per minutes is considered to be a maximum achievable.

SUMMARY OF THE INVENTION

The present disclosure is for a method for making personal hygiene absorbent articles comprising the steps of: forming a continuous supply of absorbent cores oriented in cross-machine direction; turning two or more of the absorbent cores from the cross-machine direction into a machine direction; dividing the supply of reoriented absorbent cores into two or more sub-lines; and assembling the absorbent cores on each of the multiple sub-lines in machine direction with further article elements.

The steps of turning the absorbent cores in machine direction and dividing the supply of absorbent cores into two or more sub-lines may be done separately (e.g. alternately left and right in the machine direction) but it can be advantageous that these steps are performed simultaneously. To this effect, in a second aspect, the disclosure relates also to an apparatus which can perform the steps of turning a supply of absorbent cores, optionally partially assembled with other article elements, from a cross-machine direction into a machine direction orientation and simultaneously dividing these absorbent cores along two or more multiple sub-lines for further conversion into a finished article.

An apparatus for turning a continuous supply of absorbent cores orientated in cross machine direction into a machine-direction orientation and simultaneously dividing the supply of absorbent cores into two or more sub-lines. The apparatus may comprise a plurality of turning plates and a means for reversibly transferring the turning plates from a core pick-up point to a core release point. Each of the turning plate being mounted rotationally on an axis such that the absorbent cores are re-orientated from a cross-machine direction at the pick-up point to the machine direction at the release point whilst being held on the turning plates. Each turning plate comprises means for picking up, holding and releasing two or more absorbent cores simultaneously.

DETAILED DESCRIPTION OF THE INVENTION

Figure 1:
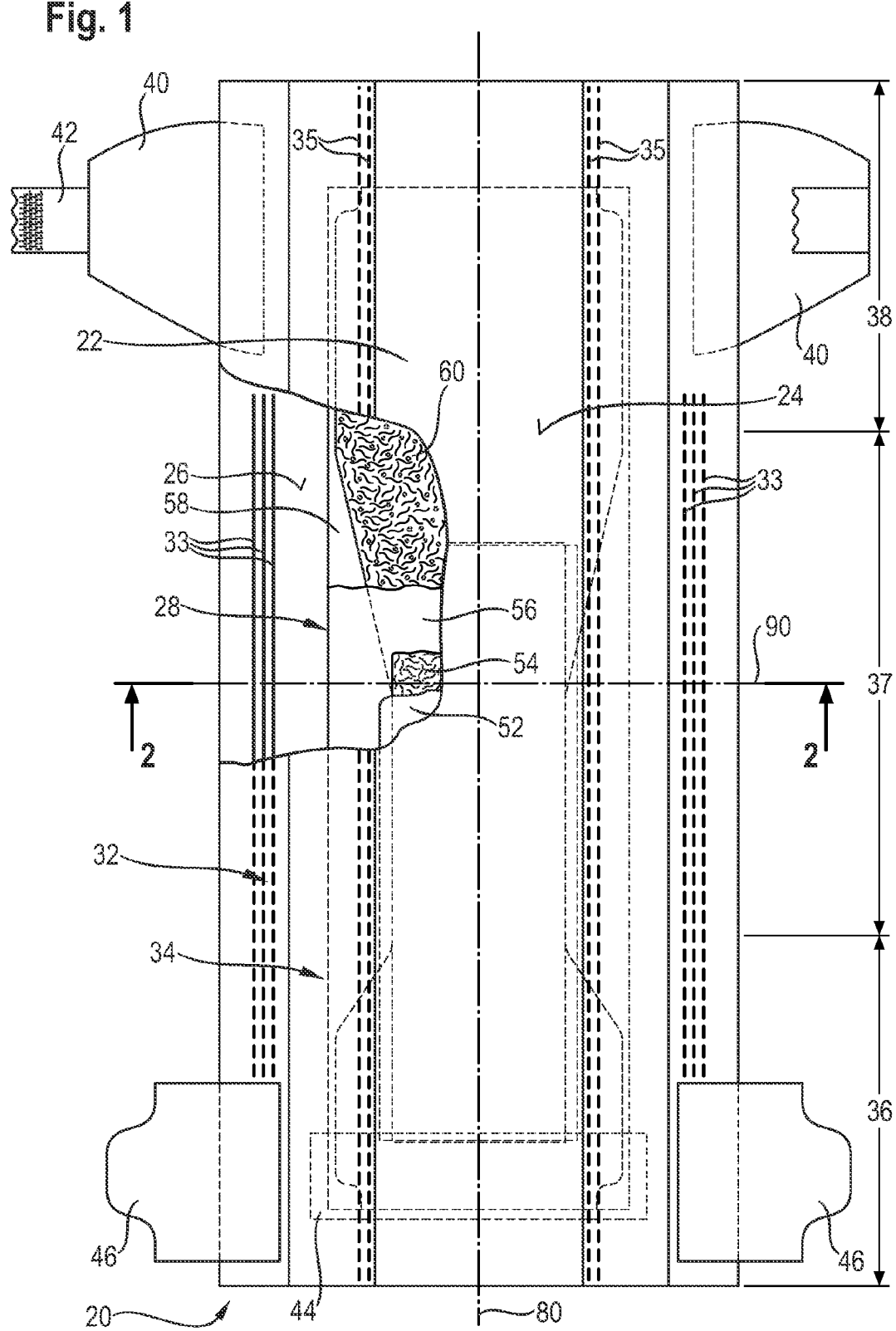
FIG. 1 is a top view of an exemplary absorbent article, in this case a diaper, partially showing the inner layers.

The following definitions may be useful in understanding the present disclosure.

As used herein, the term "absorbent article" refers to devices which absorb and contain body exudates and, more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as absorbent articles (i.e., they are intended to be discarded after a single use and to be recycled, composted or otherwise discarded in an environmentally compatible manner).

A "unitary" absorbent article refers to absorbent articles which are formed of separate parts united together to form a coordinated entity so that they do not require separate manipulative parts like a separate holder and/or liner. An exemplary configuration of a unitary absorbent article of the present disclosure is the disposable diaper 20 shown in FIG. 1. As used herein, the term "diaper" refers to an absorbent article generally worn by infants and incontinent persons about the lower torso so as to encircle the waist and legs of the wearer and that is specifically adapted to receive and contain urinary and fecal waste. As used herein, the term "diaper" also includes "training pants" which refers to refers to disposable garments having a waist opening and leg openings designed for infant or adult wearers. The present disclosure is also applicable to other absorbent articles such as incontinence briefs, incontinence undergarments, absorbent inserts, diaper holders and liners, feminine hygiene garments, wipes, mops, bandages and the like.

"Absorbent core" means a structure disposed between a topsheet and a backsheet of an absorbent article for absorbing and containing liquid received by the absorbent article. For the present disclosure, the absorbent core does not include the topsheet, the backsheet and (if present) the acquisition system of the absorbent article. Further details of the construction of typical absorbent core are discussed below.

A "nonwoven web" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding and airlaying. The basis weight of nonwoven webs is usually expressed in grams per square meter (g/m$^2$).

"Comprise," "comprising," and "comprises" are open ended terms, each specifies the presence of what follows, e.g., a component, but does not preclude the presence of other features, e.g., elements, steps, components known in the art, or disclosed herein.

By "converting line" it is meant the assembly line where absorbent articles are assembled into finished articles. Modern converting lines are highly automated and efficient and can usually assemble in one continuous process all the elements of the absorbent articles. The absorbent articles in their various stages of completion follow a path which is known in the art as the "machine direction" or MD while the perpendicular direction is called "cross-machine" direction or CD. In general, absorbent articles are made in machine direction, which means that the length of the article is oriented in machine direction and its width in cross-machine direction during the various stages of assembly. However it is also known to make absorbent articles in cross-direction, or changing the orientation of the articles during processing from one direction to the other so that the article is partially made in machine direction and partially in cross-machine direction, as indicated in the background section above.

Absorbent Article

A typical absorbent article in the form of a diaper 20 is represented in FIG. 1. In more details, FIG. 1 is a plan view of an exemplary diaper 20, which can be made using the method of the disclosure, in a flat-out state, with portions of the structure being cut-away to more clearly show the construction of the diaper 20. This diaper 20 is shown for illustration purpose only as the disclosure may used for making a wide variety of diapers or other absorbent articles. In the following, the term diaper will be used for convenience, being understood that what follows can be applied to any other type of absorbent articles unless specifically excluded.

Figure 2:
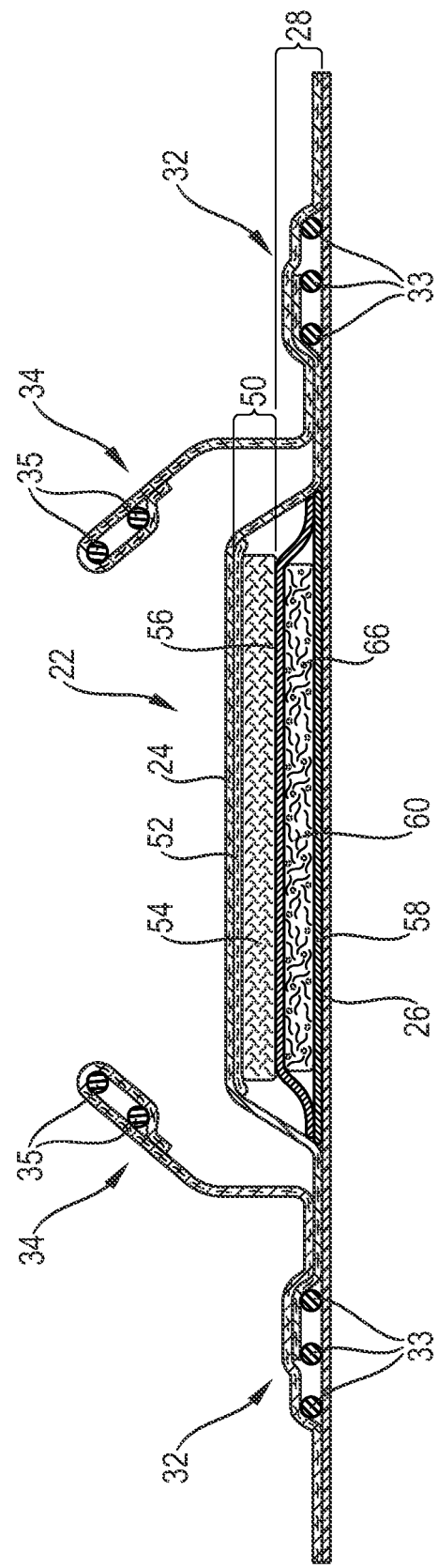
FIG. 2 is a cross-section view of the article of FIG. 1.
Figure 3:
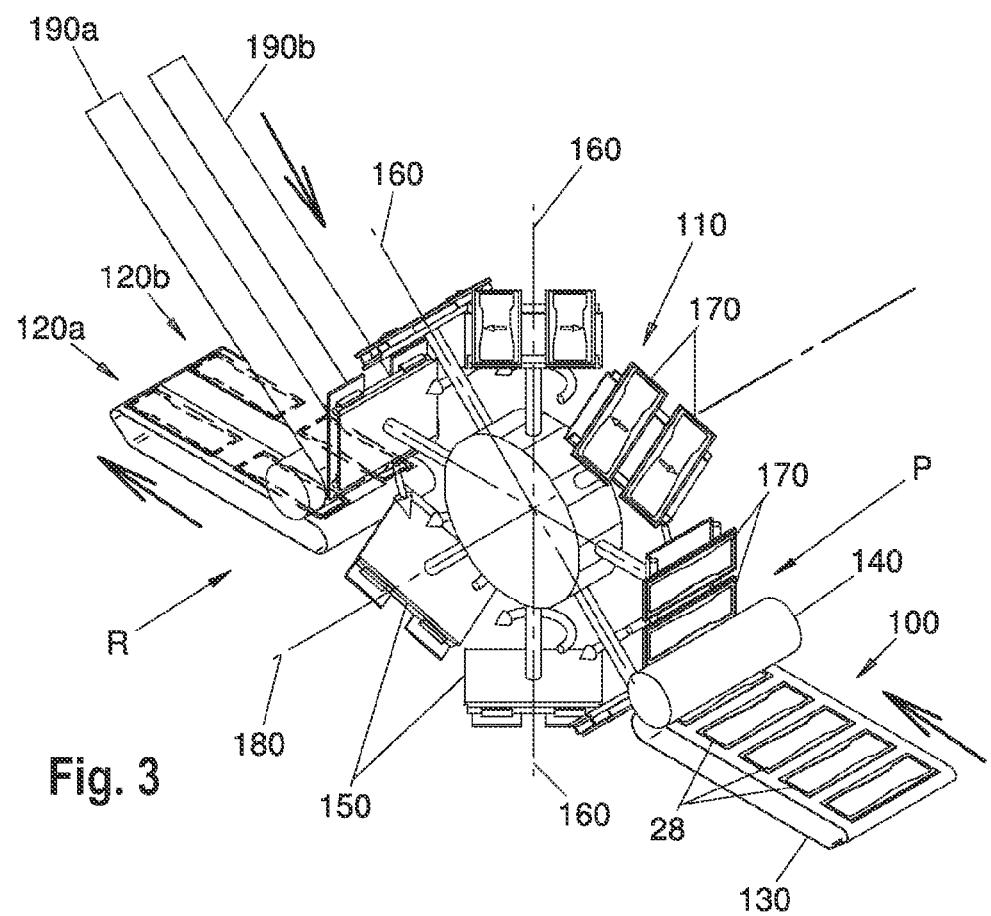
FIG. 3 is a schematic perspective view of an apparatus performing a method according to the disclosure.
Figure 4:
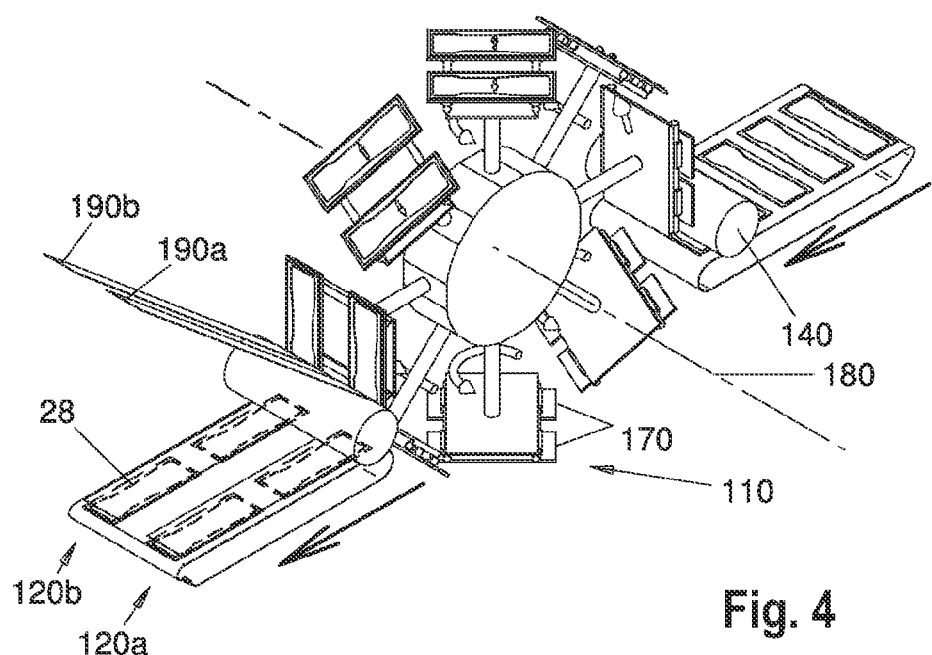
FIG. 4 is a schematic perspective view as in FIG. 3 from a different angle.
Figure 5:
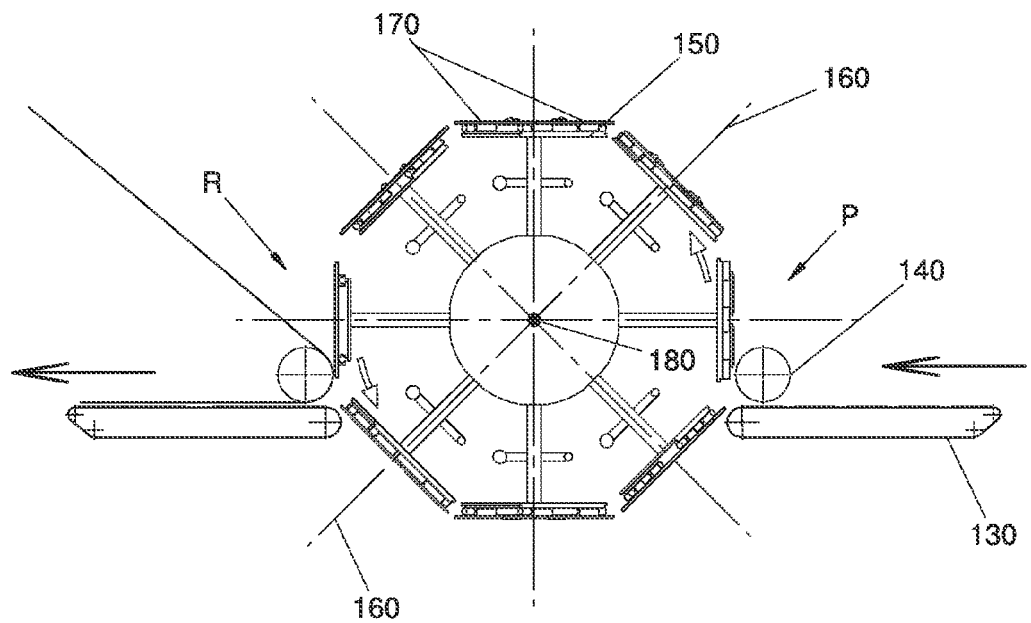
FIG. 5 is a side view of the device of FIG. 4.
Figure 6:
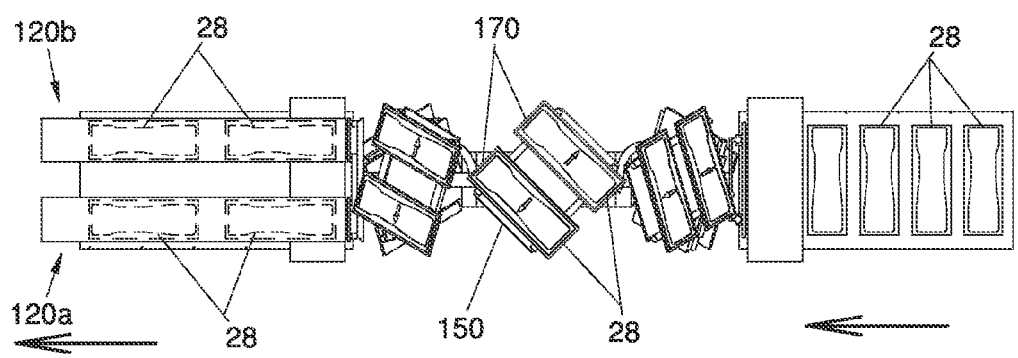
FIG. 6 is a top view of the device of FIG. 5.

As shown in FIGS. 1 and 2, the absorbent article, here a diaper, can comprise a liquid pervious topsheet 24, a liquid impervious backsheet 26, an absorbent core 28 which is positioned between at least a portion of the topsheet 24 and the backsheet 26, an acquisition system 50, elasticized leg cuffs 32 and barrier leg cuffs 34, and a fastening system which can comprise adhesive tabs 42 cooperating with a landing zone 44. The diaper may also comprise other elements, which are not represented, such as a back elastic waist feature, a front elastic waist feature, side panels, transverse barriers or a lotion application.

The diaper 20 as shown in FIG. 1 can be notionally divided in a first waist region 36, a second waist region 38 opposed to the first waist region 36 and a crotch region 37 located between the first waist region 36 and the second waist region 38 (the first and second waist regions each corresponding to about 30% of the length of the diaper and the crotch region the remaining 40%). The longitudinal centerline 80 is the imaginary line separating the diaper along its length in two equal halves. The transversal centerline 90 is the imagery line perpendicular to the longitudinal line 80 in the plane of the flattened out diaper and going through the middle of the length of the diaper. The periphery of the diaper 20 is defined by the outer edges of the diaper 20. The longitudinal edges of the diaper may run generally parallel to the longitudinal centerline 80 of the diaper 20 and the end edges run between the longitudinal edges generally parallel to the transversal centerline 90 of the diaper 20.

The chassis 22 of the diaper 20 comprises the main body of the diaper 20. The chassis 22 comprises the absorbent core 28 and an outer covering including the topsheet 24 and/or the backsheet 26. The majority of diapers are unitary, and the chassis 22 comprises the main structure of the diaper with other features such as back ears 40 and/or barrier cuffs 34 attached to form the composite diaper structure. The topsheet 24, the backsheet 26, and the absorbent core 28 may be assembled in a variety of well known configurations, in particular by gluing or heat embossing. Exemplary diaper configurations are described generally in U.S. Pat. Nos. 3,860,003; 5,221,274; 5,554,145; 5,569,234; 5,580,411; 6,004,306.

Backsheet

The backsheet 26 is generally that portion of the diaper 20 positioned adjacent the garment-facing surface of the absorbent core 28 and which prevents the exudates absorbed and contained therein from soiling articles such as bedsheets and undergarments. The backsheet 26 is typically impervious to liquids (e.g. urine). The backsheet may for example be or comprise a thin plastic film such as a thermoplastic film having a thickness of about 0.012 mm to about 0.051 mm. Exemplary backsheet films include those manufactured by Tredegar Corporation, based in Richmond, Va., and sold under the trade name CPC2 film. Other suitable backsheet materials may include breathable materials which permit vapors to escape from the diaper 20 while still preventing exudates from passing through the backsheet 26. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va. and sold under the designation EXAIRE, and monolithic films such as manufactured by Clopay Corporation, Cincinnati, Ohio under the name HYTREL blend P18-3097. Some breathable composite materials are described in greater detail in PCT Application No. WO 95/16746 published on Jun. 22, 1995 in the name of E. I. DuPont; U.S. Pat. No. 5,938,648 to LaVon et al., U.S. Pat. No. 4,681,793 to Linman et al., U.S. Pat. No. 5,865,823 to Curro; and U.S. Pat. No. 5,571,096 to Dobrin et al, U.S. Pat. No. 6,946,585 B2 to London Brown.

The backsheet 26 may be joined to the topsheet 24, the absorbent core 28 or any other element of the diaper 20 by any attachment means known in the art (as used herein, the term "joined" encompasses configurations whereby an element is directly secured to another element by affixing the element directly to the other element, and configurations whereby an element is indirectly secured to another element by affixing the element to intermediate member(s) which in turn are affixed to the other element). For example, the attachment means may include a uniform continuous layer of adhesive, a patterned layer of adhesive, or an array of separate lines, spirals, or spots of adhesive. Suitable attachment means comprises an open pattern network of filaments of adhesive as disclosed in U.S. Pat. No. 4,573,986. Other suitable attachment means include several lines of adhesive filaments which are swirled into a spiral pattern, as is illustrated by the apparatus and methods shown in U.S. Pat. No. 3,911,173, U.S. Pat. No. 4,785,996; and U.S. Pat. No. 4,842,666. Adhesives which have been found to be satisfactory are manufactured by H. B. Fuller Company of St. Paul, Minn. and marketed as HL-1620 and HL 1358-XZP. Alternatively, the attachment means may comprise heat bonds, pressure bonds, ultrasonic bonds, dynamic mechanical bonds, or any other suitable attachment means or combinations of these attachment means as are known in the art.

Topsheet

The topsheet 24 is normally positioned adjacent body surface of the absorbent core 28 and may be joined thereto and/or to the backsheet 26 by any attachment means known in the art. Suitable attachment means are described above with respect to means for joining the backsheet 26 to other elements of the diaper 20. Usually, the topsheet 24 and the backsheet 26 are joined directly to each other in some locations (e.g., on or close to the periphery of the diaper) and are indirectly joined together in other locations by directly joining them to one or more other elements of the diaper 20.

The topsheet 24 may be compliant, soft-feeling, and non-irritating to the wearer's skin. Further, at least a portion of the topsheet 24 is liquid pervious, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. If the topsheet 24 includes fibers, the fibers may be spunbond, carded, wet-laid, meltblown, hydroentangled, or otherwise processed as is known in the art, in particular spunbond PP nonwoven. One suitable topsheet 24 comprising a web of staple-length polypropylene fibers is manufactured by Veratec, Inc., a Division of International Paper Company, of Walpole, Mass. under the designation P-8.

Suitable formed film topsheets are described in U.S. Pat. No. 3,929,135; U.S. Pat. No. 4,324,246; U.S. Pat. No. 4,342,314; U.S. Pat. No. 4,463,045; and U.S. Pat. No. 5,006,394. Other suitable topsheets 30 may be made in accordance with U.S. Pat. No. 4,609,518 and U.S. Pat. No. 4,629,643 issued to Curro et al. Such formed films are available from The Procter & Gamble Company of Cincinnati, Ohio as "DRI-WEAVE" and from Tredegar Corporation, based in Richmond, Va., as "CLIFF-T".

Any portion of the topsheet 24 may be coated with a lotion as is known in the art. Examples of suitable lotions include those described in U.S. Pat. No. 5,607,760; U.S. Pat. No. 5,609,587; U.S. Pat. No. 5,635,191; U.S. Pat. No. 5,643,588; U.S. Pat. No. 5,968,025; and U.S. Pat. No. 6,716,441. The topsheet 24 may also include or be treated with antibacterial agents, some examples of which are disclosed in PCT Publication WO 95/24173. Further, the topsheet 24, the backsheet 26 or any portion of the topsheet or backsheet may be embossed and/or matte finished to provide a more cloth like appearance.

The topsheet 24 may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" from the article is increased. Typically, the area of the apertures at the surface of a diaper may have an area of between about 10 $cm^2$ and about 50 $cm^2$, in particular between about 15 $cm^2$ and 35 $cm^2$. Examples of apertured topsheet are disclosed in U.S. Pat. No. 6,632,504, assigned to BBA NONWOVENS SIMPSONVILLE. WO 2011/163582. Typical diaper topsheets have a basis weight of from about 10 to about 21 gsm, in particular between from about 12 to about 18 gsm but other basis weight are possible.

Absorbent Core

Absorbent articles typically comprise an absorbent core whose purpose is to absorb and retain liquids such as urine and other certain body exudates. The absorbent core 28 may be made from a wide variety of materials assembled in different ways, as is known in the art. The absorbent core will typically comprise at least one layer of absorbent material 60, which may be sandwiched or encapsulated between one or two substrate layers 56, 58. Typical absorbent materials may be selected from the group consisting of cellulose fibers, modified cellulose fibers (e.g. cross-linked cellulose fibers), superabsorbent polymeric materials, absorbent foams, tissues, and combinations thereof. Commonly used materials for disposable diapers and other absorbent articles include comminuted wood pulp, which is generally referred to as airfelt, and its mixtures with superabsorbent polymers (SAP), also called absorbent gelling materials (AGM) in particulate form. Such a core is exemplary shown in FIG. 1 and FIG. 2 with the AGM particles 66 represented in a schematic way. Possible substrate layers 56, 58 are discussed further below.

"Superabsorbent polymers" as used herein refer to absorbent material which are cross-linked polymeric materials that can absorb at least 10 times their weight of an aqueous 0.9% saline solution as measured using the Centrifuge Retention Capacity test (Edana 441.2-05), at least 15 times the weight of the superabsorbent polymer, or at least 20 times the weight of the superabsorbent polymer. The superabsorbent polymer can be in particulate form so as to be flowable in the dry state. Typical particulate absorbent polymer materials are made of poly(meth)acrylic acid polymers. However, e.g., starch-based particulate absorbent polymer material may also be used.

The superabsorbent polymer particles useful for the present disclosure may be of numerous shapes. The term "particles" refers to granules, fibers, flakes, spheres, powders, platelets and other shapes and forms known to persons skilled in the art of superabsorbent polymer particles. In some exemplary configurations, the superabsorbent polymer particles can be in the shape of fibers, i.e. elongated, acicular superabsorbent polymer particles. In those exemplary configurations, the superabsorbent polymer particles fibers have a minor dimension (i.e. diameter of the fiber) of less than about 1 mm, less than about 500 µm, or less than 250 µm down to 50 µm. The length of the fibers may be in the range of about 3 mm to about 100 mm. The fibers can also be in the form of a long filament that can be woven.

Typically, superabsorbent polymer particles are spherical-like particles. According to the present disclosure and in contrast to fibers, "spherical-like particles" have a longest and a smallest dimension with a particulate ratio of longest to smallest particle dimension in the range of 1-5, where a value of 1 would equate a perfectly spherical particle and 5 would allow for some deviation from such a spherical particle. The superabsorbent polymer particles may have a particle size of less than 850 µm, or from 50 to 850 µm, or from 100 to 500 µm, or from 150 to 300 µm, as measured according to EDANA method WSP 220.2-05. Superabsorbent polymer particles having a relatively low particle size help to increase the surface area of the absorbent material which is in contact with liquid exudates and therefore support fast absorption of liquid exudates.

The superabsorbent polymer particles useful in the present disclosure include a variety of water-insoluble, but water-swellable polymers capable of absorbing large quantities of fluids. Such polymers materials are generally known in the art.

Suitable superabsorbent polymer particles may for example be obtained from inverse phase suspension polymerizations as described in U.S. Pat. No. 4,340,706 and U.S. Pat. No. 5,849,816, or from spray or other gas-phase dispersion polymerizations such as described in U.S. Patent Applications Nos. 2009/0192035; 2009/0258994; and 2010/0068520. In some exemplary configurations, suitable superabsorbent polymer particles may be obtained by current state of the art production processes as described, for example, in WO 2006/083584.

The surface of the superabsorbent polymer particles may be coated, for example a cationic polymer. Cationic polymers can include polyamine or polyimine materials. In some exemplary configurations, the superabsorbent polymer particles may be coated with chitosan materials such as those disclosed in U.S. Pat. No. 7,537,832 B2. In some other exemplary configurations, the superabsorbent polymer particles may comprise mixed-bed Ion-Exchange absorbent polymers such as those described in WO 99/34841 and WO 99/34842.

The absorbent core 28 may be manufactured in a wide variety of sizes and shapes (e.g. rectangular, hourglass or dog-bone, "T"-shaped, asymmetric, etc.). The configuration and construction of the absorbent core 28 may also be varied (e.g. the absorbent core(s) or other absorbent structure(s) may have varying caliper zones, hydrophilic gradient(s), a superabsorbent gradient(s), or lower average density and lower average basis weight acquisition zones; or may comprise one or more layers or structures). Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; and 5,387,207. The absorbent core may comprise a mixture of absorbent fibers and superabsorbent material (SAP) as is usual in the art or may be free of absorbent fibers ("airfelt free").

Airfelt-Free Core

Diapers with a so-called "airfelt-free" core, in which the core comprises a layer of AGM particles immobilized by fibrous glue and substantially free of airfelt are known. Examples of such cores are, for example, disclosed in U.S. Pat. No. 5,562,645 (Tanzer et al.); U.S. Pat. No. 7,750,203 (Busam et al.); and U.S. Patent Publication No. 2008/0312622; U.S. Patent Publication No. 2008/0312617A1; U.S. Patent Publication No. 2008/0312617A1 (all Hundorf et al.). The core may also comprise a layer of AGM and a layer of airfelt mixed with AGM, as for example disclosed in U.S. Pat. No. 5,830,202 (Bogdanski et al.). In such exemplary configurations, the absorbent core may comprise more than 80% of superabsorbent polymer materials by weight of absorbent material, more than 90%, more than 95%, or more than 98%. The absorbent material of the absorbent core may also consist solely of particulate absorbent polymer material. The absorbent material may comprise less than 10% of cellulose fibers by weight of the absorbent material or may even be substantially cellulose free (i.e. less than 1% cellulose). In these exemplary configurations wherein the absorbent material 60 is substantially cellulose free, the absorbent material 60 may have a density greater than about 0.4 $g/m^3$, greater than about 0.5 $g/m^3$, or greater than about 0.6 $g/m^3$.

Desirably, the superabsorbent polymer particles 66, even in the swollen state, i.e., when liquid has been absorbed, do not substantially obstruct the liquid flow throughout the material, especially when the material has a permeability, as expressed by the saline flow conductivity (SFC) of the absorbent polymer material, of greater than about 10, 40, 80, 100, 110, 120, 150, or $200 \times 10^{-7}$ $cm^3 \cdot sec/g$ and a centrifuge retention capacity (CRC) of greater than about 20 g/g, greater than about 25 g/g, and/or less than about 40 g/g, less than about 35 g/g. The absorbent particulate polymer material may have a saline flow conductivity greater than about $100 \times 10^{-7}$ $cm^3 \cdot sec/g$ and a centrifuge retention capacity of greater than about 20 g/g. The absorbent particulate polymer material may have a saline flow conductivity greater than about $70 \times 10^{-7}$ $cm^3 \cdot sec/g$ and a centrifuge retention capacity of greater than about 25 g/g. Saline flow conductivity is a parameter well recognized in the art and is to be measured in accordance with the test disclosed in U.S. Patent Publication No. 2007/219521 filed on Mar. 15, 2007. Centrifuge retention capacity is another parameter well recognized in the art and is to be measured in accordance with the test disclosed in WO 2007/047598.

The superabsorbent polymer particles may be present in a basis weight of at least about 200 $g/m^2$, at least about 400 $g/m^2$, or at least about 600 $g/m^2$. The basis weight may be desirably less than about 2000 $g/m^2$ to maintain flexibility.

The absorbent material 60 may have a relatively narrow width in the crotch area of the absorbent article for increased wearing comfort. Hence, the absorbent material 60 may have a width as measured along a transverse line which is positioned at equal distance to the front edge and the rear edge of the absorbent article, which is less than about 100 mm, 90 mm, 80 mm, 70 mm, 60 mm or even less than about 50 mm.

It has been found that, for most absorbent articles such as diapers, the liquid discharge occurs predominately in the front half of the diaper. It may be desirable that the front half of the absorbent core comprise most of the absorbent capacity of the core. Thus, according to certain exemplary configurations, the front half of the absorbent core may comprise more than about 60% of the superabsorbent polymer particles, or more than about 65%, 70%, 75%, 80%, 85%, or 90% of the superabsorbent polymer particles.

Core Cover and Dusting Layer

The absorbent material 60 of the absorbent core 28 can be contained or wrapped in one or more substrates in order to facilitate manipulation and/or reduce the risk of leakage of the absorbent material outside of the diapers. The absorbent material 60 may for example be sandwiched between two layers of materials which are bound at their periphery, as shown on FIG. 2. The upper layer 56 can be referred to as a core cover while the lower layer 58 can be referred as a dusting layer. The substrate may also be made of one layer wrapped around the absorbent material. The one or more substrate may be sealed along the whole of periphery of the core or parts thereof, for example along the longitudinal borders of the core, typically by gluing or heat/pressure bonding. The core cover may also be C-wrapped around the core's absorbent material 60 and the dusting layer 58 positioned between the core's absorbent material 60 and the wrapped flaps of the core cover 56. Both upper and lower layers are typically made of a nonwoven layer. Of course the core cover should be fluid permeable and may receive a surface treatment to increase its hydrophilicity.

The core cover 58 and/or dusting layer 56 may be for example spunmelt PP nonwovens, in particular those having an SMMS structure, and having a basis weight range of about 5 gsm to 15 gsm, in particular 8 gsm. Other suitable materials are for examples disclosed in U.S. Patent Publication Nos. 2011/0268932 A1; 2011/0319848 A1; and 2011/0250413 A1 for bond pattern improvements for general description.

Acquisition System

The diaper 20 may include one or more sublayer(s) disposed between the topsheet 24 and the backsheet 26 in addition to the absorbent core 28, as is known in the art. The sublayer may be any material or structure capable of accepting, storing or immobilizing bodily exudates. In particular, the diapers may comprise an acquisition system between the topsheet 24 and the absorbent core 28. The acquisition system 50 may be in direct contact with the absorbent core. The acquisition system 50 is desirable to quickly acquire the fluid and distribute across a larger area to maximize the use of the storage capacity of the core. The acquisition system 50 may function to receive a surge of liquid, such as a gush of urine. In other words, the acquisition system 50 may serve as a temporary reservoir for liquid until the absorbent core 14 can absorb the liquid.

The acquisition system 50 may comprise a single layer of an absorbent nonwoven or comprise multiple layers. The acquisition system may for example be a laminate of different nonwovens or an integral layer comprising different sub-layers for example airlaid layers integrated to form an unitary acquisition system as is known in the art. In an exemplary configuration, the acquisition system may comprise an upper acquisition layer 52 and a lower acquisition 54 layer. The acquisition system 50 may for example comprise as upper acquisition layer 52 comprising a nonwoven layer made of natural or synthetic fibers which may be treated by a surfactant to quickly acquire the fluid, and underneath a lower acquisition layer 54, which may comprise cross-linked cellulose fibers, to distribute the fluid across a larger surface, as will be discussed in more details below.

Upper Acquisition Layer

The upper acquisition layer 52 may typically be or comprise a non-woven material. Examples of suitable non-woven materials include, but are not limited to SMS or SMMS material, comprising a spunbonded, a melt-blown and a further spunbonded layer and alternatively a carded chemical-bonded nonwoven. The non-woven material may be latex bonded. Exemplary upper acquisition layers 52 are disclosed in U.S. Pat. No. 7,786,341. Carded, resin-bonded nonwovens may be used, in particular where the fibers used are solid round PET staple fibers (50/50 or 40/60 mix of 6 denier and 9 denier fibers). An exemplary binder is a butadiene/styrene latex.

The non-wovens may be porous. As polymers used for nonwoven production may be inherently hydrophobic, they may be coated with hydrophilic coatings. One way to produce nonwovens with durably hydrophilic coatings is via applying a hydrophilic monomer and a radical polymerization initiator onto the nonwoven, and conducting a polymerization activated via UV light resulting in monomer chemically bound to the surface of the nonwoven. Exemplary methods are described in U.S. Patent Publication No. 2005/159720. Another way to produce nonwovens with durably hydrophilic coatings is to coat the nonwoven with hydrophilic nanoparticles. Exemplary methods are described in U.S. Pat. No. 7,112,621 to Rohrbaugh et al. and in WO 02/064877.

Further useful non-wovens are described in U.S. Pat. No. 6,645,569 to Cramer et al.; U.S. Pat. No. 6,863,933 to Cramer et al.; U.S. Pat. No. 7,112,621 to Rohrbaugh et al.; U.S. Patent Publication No. 2003/148684 to Cramer et al.; and U.S. Patent Publication No. 2005/008839 to Cramer et al.

The upper acquisition layer 52 may be stabilized by a latex binder, for example a styrene-butadiene latex binder (SB latex). Processes for obtaining such lattices are known, for example, from EP0149880 (Kwok) and U.S. Patent Publication No. 2003/105190 (Diehl et al.). In certain exemplary configurations, the binder may be present in the upper acquisition layer 52 in excess of about 12%, about 14% or about 16% by weight. SB latex is available under the trade name GENFLO™ 3160 (OMNOVA Solutions Inc.; Akron, Ohio).

Lower Acquisition Layer

The acquisition system 50 may comprise chemically cross-linked cellulosic fibers, in particular in a lower acquisition layer 54. Exemplary chemically cross-linked cellulosic fibers are disclosed in U.S. Pat. No. 5,137,537, WO 95/34329 and U.S. Patent Publication No. 2007/118087. Polycarboxylic acids such as citric acid may be used as exemplary cross-linking agents. The chemically cross-linked cellulosic fibers may be cross-linked with between about 0.5 mole % and about 10.0 mole % of a $C_2$ to $C_9$ polycarboxylic cross-linking agent or between about 1.5 mole % and about 6.0 mole % of a $C_2$ to $C_9$ polycarboxylic cross-linking agent based on glucose unit. Polyacrylic acids may also be used as cross-linking agents. The cross-linked cellulosic fibers may be crimped, twisted, or curled, or a combination thereof including crimped, twisted, and curled.

Examples of lower acquisition layer 54 may comprise about 70% by weight of chemically cross-linked cellulose fibers, about 10% by weight polyester (PET), and about 20% by weight untreated pulp fibers. In another example, the lower acquisition layer 54 may comprise about 70% by weight chemically cross-linked cellulose fibers, about 20% by weight lyocell fibers, and about 10% by weight PET fibers. In another example, the lower acquisition layer 54 may comprise about 68% by weight chemically cross-linked cellulose fibers, about 16% by weight untreated pulp fibers, and about 16% by weight PET fibers. In another example, the lower acquisition layer 54 may comprise from about 90-100% by weight chemically cross-linked cellulose fibers.

Fastening System

The diaper 20 may also include a fastening system 42-44. The fastening system can be used to maintain the first waist region 36 and the second waist region 38 in a configuration so as to provide lateral tensions about the circumference of the diaper 20 to hold the diaper 20 on the wearer. The fastening system 42-44 usually comprises a fastener such as tape tabs, hook and loop fastening components, interlocking fasteners such as tabs & slots, buckles, buttons, snaps, and/or hermaphroditic fastening components, although any other known fastening means are generally acceptable. A landing zone 44 is normally provided on the first waist region 36 for the fastener to be releasably attached. Some exemplary surface fastening systems are disclosed in U.S. Pat. No. 3,848,594, U.S. Pat. No. 4,662,875; U.S. Pat. No. 4,846,815; U.S. Pat. No. 4,894,060; U.S. Pat. No. 4,946,527; U.S. Pat. No. 5,151,092; and U.S. Pat. No. 5,221,274 issued to Buell et al. An exemplary interlocking fastening system is disclosed in U.S. Pat. No. 6,432,098. The fastening system 42-44 may also provide a means for holding the article in a disposal configuration as disclosed in U.S. Pat. No. 4,963,140 issued to Robertson et al.

The fastening system may also include primary and secondary fastening systems, as disclosed in U.S. Pat. No. 4,699,622 to reduce shifting of overlapped portions or to improve fit as disclosed in U.S. Pat. No. 5,242,436; U.S. Pat. No. 5,499,978; U.S. Pat. No. 5,507,736; and U.S. Pat. No. 5,591,152.

Front and Back Ears

The diaper 20 may comprise front ears 46 and back ears 40 as is known in the art. The ears can be integral part of the chassis, for example formed from the topsheet and/or backsheet as side panel. Alternatively, as represented on FIG. 1, they may be separated element attached by gluing and/or heat embossing. The back ears 40 are advantageously stretchable to facilitate the attachment of the tabs 42 on the landing zone 40 and maintain the taped diapers in place around the baby's waist. The back ears 30 may also be elastic or extensible to provide a more comfortable and contouring fit by initially conformably fitting the diaper 20 to the wearer and sustaining this fit throughout the time of wear well past when the diaper 20 has been loaded with exudates since the elasticized ears allow the sides of the diaper 20 to expand and contract, see for example, U.S. Pat. Nos. 3,860,003 and 5,151,092.

Leg Cuffs

The diaper 20 may comprise leg cuffs 32 which provide improved containment of liquids and other body exudates. Leg cuffs 32 may also be referred to as leg bands, side flaps, barrier cuffs, or elastic cuffs. Usually each leg cuffs will comprise one or more elastic string 33, represented in exaggerated form on FIG. 2 comprised in the chassis of the diaper for example between the topsheet and backsheet in the area of the leg openings to provide an effective seal while the diaper is in use. It is also usual for the leg cuffs to comprise "stand-up" elasticized flaps (barrier leg cuffs) 34 which improve the containment of the leg regions. Each barrier leg cuff typically comprises one or more elastic strings 35.

Exemplary disposable diapers having leg cuffs are described in U.S. Pat. No. 3,860,003; U.S. Pat. No. 4,808,178; U.S. Pat. No. 4,909,803 U.S. Pat. No. 4,695,278; U.S. Pat. No. 4,795,454. In some exemplary configurations, it may be desirable to treat all or a portion of the leg cuffs 32 with a lotion, as described above.

Elastic Waist Feature

The diaper 20 may also comprise at least one elastic waist feature (not represented) that helps to provide improved fit and containment. The elastic waist feature is generally intended to elastically expand and contract to dynamically fit the wearer's waist. The elastic waist feature may extend at least longitudinally outwardly from at least one waist edge of the absorbent core 28 and generally forms at least a portion of the end edge of the diaper 20. Disposable diapers can be constructed so as to have two elastic waist features, one positioned in the first waist region 36 and one positioned in the second waist region 38. The elastic waist feature may be constructed in a number of different configurations, including those described in U.S. Pat. No. 4,515,595, U.S. Pat. No. 4,710,189, U.S. Pat. No. 5,151,092 and U.S. Pat. No. 5,221,274

Method

In a first step, the method of the disclosure involves forming a continuous supply 100 of absorbent cores 28 oriented in cross-machine direction (CD) on a converting line. Since the cores are oriented in CD, it is possible for a given speed line in m/s to supply more absorbent cores than if the cores where oriented in MD. The way the core supply 100 is formed is not critical in the context of the disclosure. Conventional core making techniques include for example airlaying of a mixture of pulp and superabsorbent polymers, but other techniques can be used for example SAP printing onto a non-woven to form airfelt free core (see e.g. WO 2006/014854, WO 2006/015141 and WO 2006/015138). In the context of feminine care sanitary articles it is also common practices to use pre-made continuous core webs which are then separated in-line.

In the method of the disclosure, the cores can be supplied in cross-machine direction at a unit speed of at least 1200 units/min. Higher speeds of at least 1500 units/min, at least 2000 units/min, at least 2500 units/min or even higher are achievable for dual-lane process, or at least 3000 units/min for triple-lane process, etc. The velocity of the supply line of the CD oriented cores may be of at least 2 m/s, at least 3 m/s, at least 4 m/s, at least 5 m/s, at least 6 m/s, at least 7 m/s, or at least 8 m/s.

Once the absorbent cores have been formed into a continuous supply in cross-machine direction, they may be assembled to other article elements, in particular such elements which are more easily attached to the absorbent core in CD direction. These elements can be for example selected from an acquisition system 50, one or more elastic waist features, a transverse barrier cuff (both not represented), a topsheet 22 or combinations thereof. The attachment of these elements to the absorbent cores 28 can be made using known conventional techniques such as gluing or crimping.

In the subsequent steps, the absorbent cores, which as indicated above may have been assembled with other article elements, are turned in machine direction and divided into multiple sub-lines. The cores can also be spaced apart ("re-pitched") at any point of the method. By "spaced apart" it is meant that a space in the cross-machine direction is provided between sub-lines. Sub-lines may be spaced apart and oriented in parallel. In an exemplary configuration of the disclosure the steps of turning the absorbent cores in machine direction and dividing the supply of absorbent cores into two or more sub-lines may be done simultaneously. It is envisioned that, alternatively, the cores may be turned and divided sequentially. For example, in order to provide two sub-lines, divided left and right in the machine direction, the absorbent cores may be turned alternately and sequentially to the left and right sub-lines.

The purpose of these steps is twofold. First, certain elements of the absorbent articles can be more easily attached to the absorbent core in machine direction. These elements include for example backsheet 26, landing zone 44, leg cuffs 32, lotion (which can be applied as longitudinal stripes). Second, because the absorbent cores were made in CD at a relatively high unit speed, this unit speed may not be manageable in MD on a single line. Dividing the flow of absorbent cores into 2 or optionally more sub-lines for further processing is an elegant way to avoid the bottleneck that would otherwise reduce the overall output of the line. For example, dividing the flow of cores into two sub-lines allows each sub-line to run at about half of the speed of the absorbent core making process. Of course the need for multiple sub-lines increases somehow the complexity and capital cost involved, however the method of the disclosure also allows producing several times the output of a conventional line. The capital cost involved using the method of the disclosure is small compared to building a complete new line because several operational units do not need to be duplicated, such as the core making unit and all the units handling the elements which are attached in CD to the absorbent core. With the disclosure, the capital cost per unit produced is thus smaller than a conventional single line converting line and delivers an ongoing productivity saving too.

The absorbent cores may be advantageously turned from CD to MD using an apparatus 110 capable of turning the continuous supply 100 of absorbent cores oriented in cross-machine direction into a machine direction orientation and simultaneously dividing the supply of absorbent cores into two or more sub-lines 120*a*, 120*b*. An exemplary configuration of such an apparatus 110 will be now described with reference to FIGS. 3 to 6. FIGS. 3 to 6 describe schematically how the steps of turning, spacing apart and dividing the cores can be performed simultaneously using an apparatus according to a second aspect of the disclosure. However the methods of the disclosure also encompass these where these steps are performed in any order. For example the cores may be first turned into machine direction and the divided into 2 or more sub-lines or vice versa using conventional devices.

As exemplary shown, on the right side of FIGS. 3 to 6, a conveyor 130 brings a supply 100 of previously formed absorbent cores 28 oriented in cross-machine direction to the turning apparatus 110. The cores may have been attached with other absorbent article elements, for example acquisition system, topsheet, any form of cuff (cross barrier, MD or a combination of both), or any kind of waist features (stretch or non stretch) and of course combination of these. The cores may also stand alone without having being attached to other elements. In the following it will not be differentiated between a core attached with other elements and a stand alone core.

The absorbent cores 28 arriving on the conveyor 130 may be individualized, i.e. are not bound to each other. If the cores were not already individualized, a cutting device (not shown) may be used to process the supply of absorbent cores in CD so that each core may be handled individually by the turning apparatus. The cutting device may also use at the same time pressure and heat to form a seam along the length of the absorbent cores by crimping certain core elements such as nonwoven core cover and/or nonwoven dusting layer if present thus encapsulating the SAP and fluff between these nonwoven layers. Such a cutting device may be a standard web-cutting unit with an in-feed and out-feed conveyor. The out-feed conveyor may then have a higher speed than the in-feed conveyor so that the cores are already spaced apart before entering the turning apparatus. A separating device may be also used for spacing the cores from another (re-pitching) before the cores are transferred to the turning apparatus. Exemplary re-pitching devices are described in U.S. Pat. No. 6,450,321; U.S. Pat. No. 6,705,453; and U.S. Pat. No. 6,811,019.

The absorbent cores are then transferred from the absorbent core supply to the turning apparatus at the core pick up point (P). As the supply of cores approaches the turning apparatus oriented in CD, the cores may be picked up by a transfer roll 140 to facilitate the placing of the cores on the turning apparatus. The cutting device, if present, may also be integrated to the transfer roll.

Figure 7A:
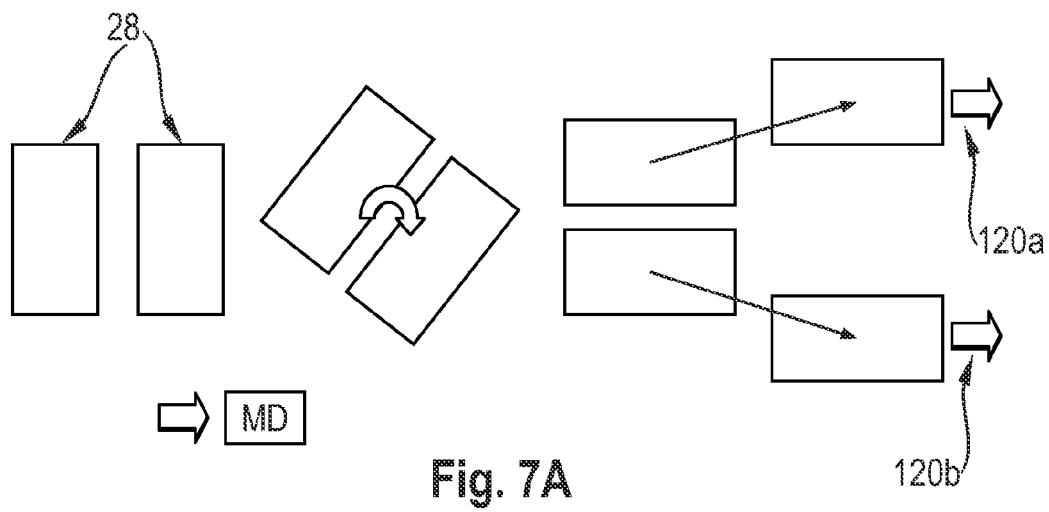
FIGS. 7A and 7B are diagrammatic representations of alternative configurations of the present disclosure.

FIG. 7A represents diagrammatically an exemplary configuration of the method of the present disclosure wherein absorbent cores 28 are first turned in pairs through 90° and subsequently spaced apart ("re-pitched") to form two sub-lines 120*a*, 120*b*.

Figure 7B:
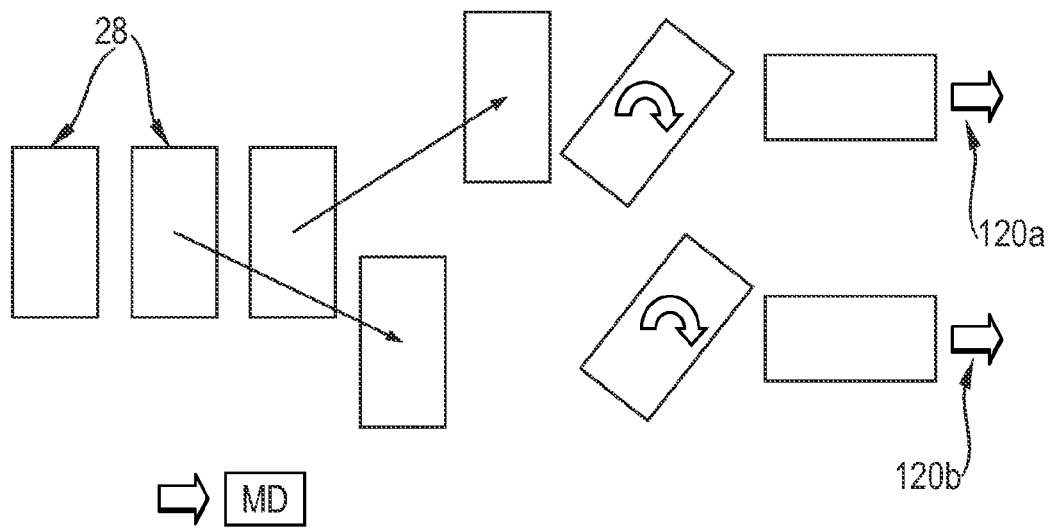

FIG. 7B represents diagrammatically an exemplary configuration of the method of the present disclosure wherein absorbent cores 28 are first spaced apart into two sub-lines, alternately to left 120*a* and right 120*b* in the machine direction, and then subsequently each absorbent core 28 is turned through 90°.

Apparatus

As will now be described in detail, the turning apparatus 110 comprises a plurality of turning plates 150 each mounted rotationally on a separate axis 160, so that the absorbent cores placed on the plate can be re-oriented from a cross-machine direction at the pick-up point into machine direction at the release point.

Each turning plate 150 comprises means for picking up, holding and releasing the absorbent cores, such as suction devices or clamp device, such as disclosed in EP 1 947 037 A1. Each turning plate is capable to pick up, hold and release at least 2 absorbent cores simultaneously. The turning plates can comprise a plurality of sub-plates 170 for picking, holding and releasing the absorbent cores. On the schematic diagrams shown in FIG. 3-7 each turning plate is shown picking up two absorbent cores, but more absorbent cores per turning plate may be considered, for example 3, 4, 5, 6 or 7.

The turning plates are then reversibly transferred from the core pick-up point (P) to a core release point (R) while the absorbent cores are re-oriented from a CD to a MD direction. Each of the turning plate can be mounted rotationally on an axis 160 as shown in the Figures so that they can rotate by 90° relative to this axis while the transfer is taking place between P and R. As represented in FIGS. 1 and 2, when viewed from above, the direction of rotation of the turning plates maybe counter-clockwise between P and R. The direction may then be inversed when the plates are brought back to P between R and P. Other rotational direction may of course be used, such as described in EP 1 947 037 A1.

A wheel 200 having a fixed axis of rotation 180 that is perpendicular to the supply of cores 100 may carry the rotational axis of the turning plates and bring the turning plates from the core pick-up point P to the core release point R, and then back from the release point R back to the pick-up point P. As shown in the figures, the rotational axis 160 of the turning plates can radially expend outwards from the center of the wheel. In the exemplary configuration shown, the radial speed of the turning plates and their distance relative to the rotating wheel axis 180 may remain constant during the revolution of the turning plates around the axis 180. It is also possible to increase the distance of the turning plates from the rotating wheel axis between the core pick-up point P and the core release point R, as this will increase at the same time the distance between the plates and may facilitate the release of the absorbent cores. Exemplary methods are disclosed in U.S. Pat. No. 4,617,082, for example. It may also be desired to increase or decrease the speed of rotation of the turning plates relative to the axis 180 between the core pick-up point and the core release-point. For example, a plurality of coaxial shafts each carrying a turning plate coupled to respective members may be used for control in rotation. The respective members for control in rotation may comprise rotating bodies such as pulleys or toothed gears. Exemplary methods are described in EP 1 947 037.

Each core may be held on each of the turning plate by an individual sub-plate 170. As shown in FIGS. 3-7, there may be at least two sub-plates for each turning plate. The sub-plates may move away from each other as the turning plate is turned on its axis to space apart the absorbent cores, as schematically represented by the opposing arrows on the sub-plates in FIGS. 3-7 between the core pick-up point and the core release point. The sub-plates can be moved apart for example using a cam-follower system driven by the rotating wheel or pneumatic cylinders controlled by the position of the turning plates on the wheel or an electric motor.

Simultaneously spacing apart the cores while re-orientating them can make it simpler to divide the cores into the multiple sub-lines. On the other hand, the cores may already be sufficiently spaced apart before entering the turning apparatus so that it is not necessary to space them apart during the turning step. For example, the absorbent cores may already be spaced apart by another unit using a spacing device as previously indicated before the cores are picked up. In this way the construction of the turning plates can be simplified as the moveable sub-plates are no longer needed. On the other hand, having a spacing device adds one source of process variation which is undesired at the high production speed considered, so that doing the spacing apart and turning step simultaneously may be advantageous. The cores may also be spaced apart after having been released from the turning apparatus when standing side-by-side in machine direction for example using two independent web-tracking tables. This may also create additional process variation compared to simultaneous turning and spacing apart.

The two or more cores now oriented in machine direction and held on the turning plates are simultaneously released at the core release point R, which is attained after half a revolution of the wheel. The cores may be released to a conveyor or may be released directly onto a receiving web 190 which takes over the transport function of the conveyor. The receiving web may be for example a backsheet material or topsheet material. This is illustrated, for example, in FIG. 3 and FIG. 5 where one receiving web 190a, 190b such as a backsheet material is present for each core. A single receiving web for all sub-lines may also be used, in that case the web can be cut along its length in machine direction further down the sub-lines.

If the two or more cores 28 released simultaneously have already been spaced apart when they are released, the receiving web may be split into the same number of sub-webs as needed for the cores as the distance between each core may be too large for a single web. The web may then come from a single roll of material which is split into 2 or more sub-webs 190a, 190b.

The absorbent cores (together with the other articles elements which may have already been attached in CD direction) are then assembled on each of the multiple sub-lines in machine direction with further article elements. In particular finished articles may thus be completed on each of the sub-lines. The further article elements assembled in machine direction can be for example selected from backsheet, landing zone, leg cuffs, lotion and combinations thereof.

Each of the multiple sub-lines may further lead to a different bagging device (not shown). This may allow for example making bags with different bag counts. On the other hand the sub-lines may be joined again into a single line, so that the partially assembled cores or finished articles can be further processed and/or brought to a single bagging device. It is also possible to divide one or more of the sub-lines again, for example to lead to two or more further bagging-devices.

Once the cores have been released from the turning apparatus at the core release point R, the turning plates are transferred back to the core pick up point while the wheel performs a second half revolution. If present the moveable sub-plates can be brought back into a closed position during this second half revolution, ready to pick-up another multiplicity of cores at the pick-up point P.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any disclosure disclosed or claimed herein or that it alone, or in any combination with any other reference or references, teaches, suggests or discloses any such disclosure. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

The invention claimed is:

1. A method for making personal hygiene absorbent articles, the method comprising the steps of:
   forming a continuous supply of absorbent cores oriented in a cross-machine direction;
   simultaneously picking up two or more absorbent cores from the continuous supply of absorbent cores;
   turning two or more of the absorbent cores from the cross-machine direction into a machine direction orientation;
   dividing the supply of reoriented absorbent cores into at least two absorbent article sub-lines by spacing apart the absorbent cores relative to one another with space in the cross-machine direction between the sub-lines, wherein the at least two absorbent article sub-lines are parallel to said machine direction; and assembling the absorbent cores on each of the multiple sub-lines in a machine direction with further article elements to substantially simultaneously define multiple absorbent articles, wherein the cores are turned in the machine direction and spaced apart simultaneously.

2. The method of claim 1 further comprising the step of assembling the absorbent cores with other article elements while the cores are oriented in the cross-machine direction.

3. The method of claim 2, wherein the other article elements assembled with the absorbent cores in the cross-machine direction include elements selected from acquisition system layer, waist band, transverse barrier cuff, topsheet and combinations thereof.

4. The method of claim 1, wherein the cores are spaced apart while orientated in the cross-machine direction, between the step of forming a continuous supply of absorbent cores and the step of turning the absorbent cores in the machine direction.

5. The method of claim 1, wherein the further article elements assembled in the machine direction include elements selected from backsheet, landing zone, leg cuffs, lotion and combinations thereof.

6. The method of claim 1, wherein the absorbent articles are diapers.

7. The method of claim 1, wherein the continuous supply of absorbent cores oriented in the cross-machine direction are transferred on a conveyor.

8. The method of claim 1, comprising transferring the continuous supply of absorbent cores to a transfer roll.

9. The method of claim 1, wherein simultaneously picking up two or more absorbent cores from the continuous supply of absorbent cores comprises positioning the two or more absorbent cores on a turning plate.

10. The method of claim 9, wherein the turning plate comprises at least two sub-plates, wherein each of the two or more absorbent cores is received by an individual sub-plate.

11. The method of claim 9, comprising rotating the turning plate about a rotational axis.

12. The method of claim 9, comprising increasing and decreasing a distance from the turning plate to a rotating wheel axis of rotation.

13. A method for making personal hygiene absorbent articles, the method comprising the steps of:

transferring a continuous supply of absorbent cores oriented in a cross-machine direction;

picking up a first absorbent core and a second absorbent core using a turning plate from the continuous supply of absorbent cores, wherein the turning plate comprises a first sub-plate and a second sub-plate;

transferring the first absorbent core and the second absorbent core onto the first sub-plate and the second sub-plate, wherein the first sub-plate and the second sub-plate are oriented in the cross-machine direction;

rotating the first sub-plate and the second sub-plate about an axis of rotation such that the first absorbent core and the second absorbent core are rotated from the cross-machine direction to a machine direction;

dividing the first sub-plate and the second sub-plate such that the space between the first absorbent core and the second absorbent core increases;

supplying the first absorbent core oriented in the machine direction to a first absorbent article sub-line for assembly into a first absorbent article; and supplying the second absorbent core oriented in the machine direction to a second absorbent article sub-line for assembly into a second absorbent article that is independent from the first absorbent article, wherein said first and second absorbent article sublines are parallel to said machine direction.

14. The method of claim 13, comprising assembling the absorbent cores on each of the first and second sub-lines in the machine direction with further article elements.

15. The method of claim 13, comprising rotating the first sub-plate and the second sub-plate about a wheel axis of rotation.

16. The method of claim 13, comprising holding the first absorbent core on the first sub-plate and holding the second absorbent core on the second sub-plate.

* * * * *